(12) United States Patent
Knapp

(10) Patent No.: US 7,354,667 B1
(45) Date of Patent: Apr. 8, 2008

(54) AROMATHERAPEUTIC ARTICLES AND METHODS OF USE THEREOF

(76) Inventor: Christine L. Knapp, 565 Shorepines Pl., Coos Bay, OR (US) 97420

( * ) Notice: Subject to any disclaimer, the term of this patent is extended or adjusted under 35 U.S.C. 154(b) by 370 days.

(21) Appl. No.: 10/705,701

(22) Filed: Nov. 12, 2003

(51) Int. Cl.
*C11D 3/50* (2006.01)

(52) U.S. Cl. .................. 428/905; 442/96; 424/490; 512/4

(58) Field of Classification Search ......... 428/905; 442/96; 424/490; 512/4
See application file for complete search history.

(56) References Cited

U.S. PATENT DOCUMENTS

| | | | | |
|---|---|---|---|---|
| 4,376,068 A | * | 3/1983 | Mookherjee et al. | 512/1 |
| 4,487,585 A | * | 12/1984 | Goldwasser | 434/259 |
| 4,528,226 A | * | 7/1985 | Sweeny | 428/40.2 |
| 6,132,830 A | * | 10/2000 | O'Halloran | 428/40.1 |
| 2004/0022990 A1 | * | 2/2004 | Sitabkhan | 428/85 |

* cited by examiner

*Primary Examiner*—Jill Warden
*Assistant Examiner*—Paul S Hyun

(57) ABSTRACT

Articles and method for utilization of aromatherapeutic agents in both entertainment and therapeutic situations or a combination thereof, the invention contemplates the disposition of aromatherapeutic agents on or in substrates of varying description such that pressure applied to such substrates causes release of the aromatherapeutic agents to thereby cause aromas from said aromatherapeutic agents to be sensed at least by a user of the articles. Aromatherapeutic agents can be encapsulated and caused to adhere to a substrate having low-tack adhesive on at least portions thereof such that the substrate can be removable and replaceably attached to an object intended to be struck or peeled by a user to release the encapsulated aromatherapeutic agent. Aromatherapteutic agents carried by an appropriate carrier can be placed in or on a projectile to be thrown against an object causing release for an intended affect.

13 Claims, 5 Drawing Sheets

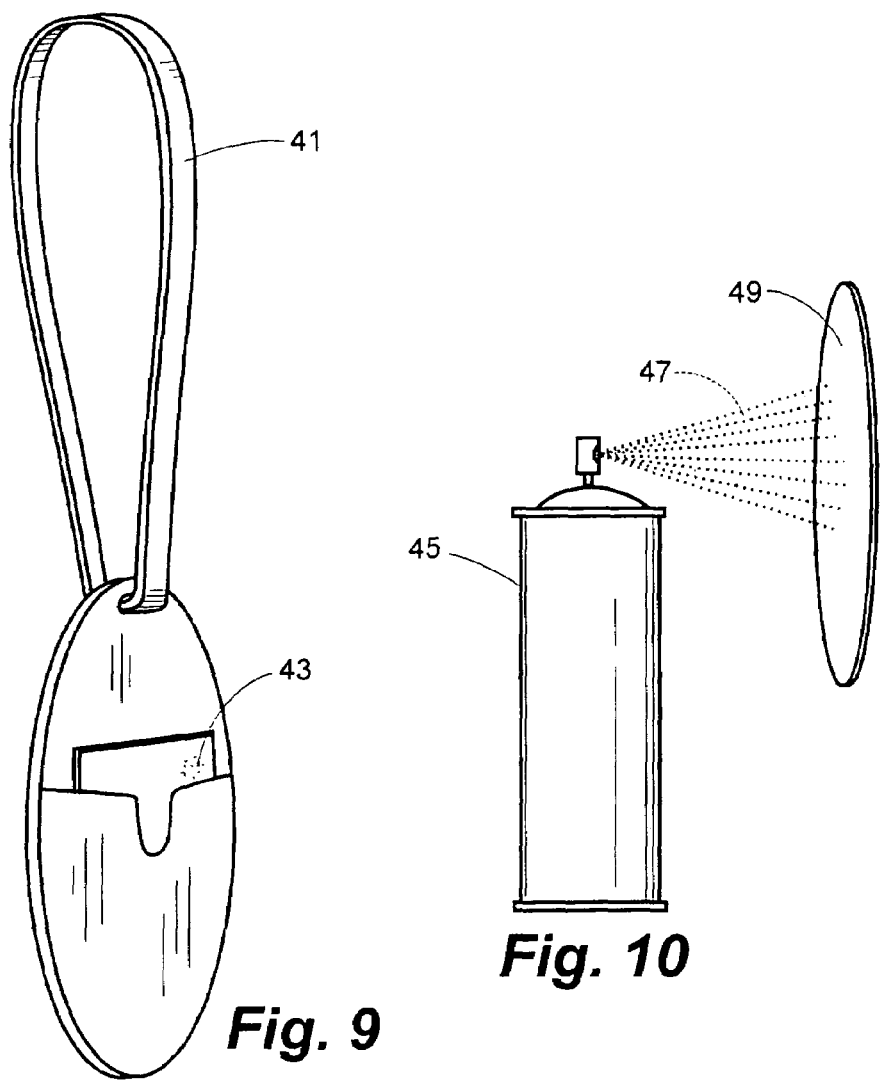
Fig. 9
Fig. 10
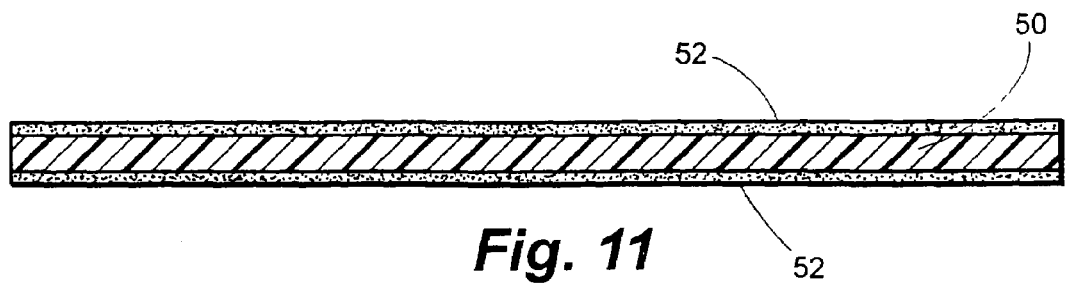
Fig. 11

AROMATHERAPEUTIC ARTICLES AND METHODS OF USE THEREOF

BACKGROUND OF THE INVENTION

1. Field of the Invention

The invention relates generally to the use of aromatherapeutic agents and particularly to articles and methods of use of such articles bearing aromatherapeutic agents for timely release of such agents to produce an entertainment and/or therapeutic affect.

2. Description of the Prior Art

Aromatherapeutic agents of varying kind have been known to have therapeutic affects historically. In relatively recent times, such agents have found utility for more than mere fanciful applications and are presently used in clinical situations for perceived therapeutic value. A primary method for delivering such agents to the olfactory senses of users has been incorporation into objects such as candles, soaps and the like, which, on use in a normally intended manner, cause an included aromatherapeutic agent to be released into an environmental space within which the article is used. This kind of use almost certainly precedes recorded history. The nature of those aromatherapeutic agents used in such situations have varied from single fragrances intended to be pleasant to the senses to specific compounds and materials believed to have calming affects on individuals having the opportunity to sense the aromas so produced. The art is replete in the literature and in previously issued patents with particular materials capable of providing perceived aromatherapeutic effects when incorporated into candles, soaps, or when delivered by other aroma delivery systems.

The art has also intended the encapsulation of fragrant materials in microcapsules and the like wherein such microcapsules have been adhered to substrates of varying description and then intentionally disrupted to break open the microcapsules in order to release fragrance into the air surrounding the disrupted microcapsules. U.S. Pat. No. 4,493,869 to Sweeny et al provides one example of such a teaching, the disclosure of this patent being incorporated hereinto by reference. In this patent, a planar substrate formed of a film or sheet material has an adhesive formed on one side so that the substrate can be adhered to a desired object. The opposite side of the substrate of Sweeny et al has microcapsules adhered thereto, the microcapsules being formed of shells of polymeric materials such as urea-formaldehyde resin within which a fragrant material is enclosed. The materials from which the encapsulating shells of Sweeny et al can be formed can vary widely similarly to the permissible variation of such encapsulating shells in the practice of the present invention. In the practice of the Sweeny et al invention, the encapsulated fragrant materials preferably take the form of a material having some relationship to a visible image formed on the substrate. As an example, an image of a bunch of grapes formed on the Sweeny et al substrate is coupled with the encapsulation of a material having the fragrance of grapes such that disruption of the microcapsules such as by scratching or the like causes the aroma of grapes to be emitted from the disrupted microcapsules. On dissipation of the resulting aroma, other microcapsules can be disrupted to refresh the emitted aroma, the intent of the use of the Sweeny et al article being the novelty of the experience.

Even though the use of prior art articles such as is disclosed by Sweeny et al as noted above have produced pleasurable effects for users, the prior art has not previously provided particular articles and methods of their use that permit realization of the benefits of aromatherapeutic agents in situations wherein entertainment and/or therapeutic benefits can occur. The invention thus intends the effective and efficient utilization of aromatherapeutic agents through incorporation of such agents in articles and methods of use of such articles to cause benefits to a user and to others subjected to use of the articles.

SUMMARY OF THE INVENTION

The invention provides articles and methods for use of such articles wherein an aromatherapeutic agent is disposed on or in an object in a quiescent states albeit subject to a percussive effect sufficient to release aromatic compounds from the aromatherapeutic agent. As one example, the aromatherapeutic agent can be disposed on a wall poster, a photograph or other image-bearing article so that a projectile thrown against the poster causes release of aromas from the aromatherapeutic agent. In particular, a poster such as is used as a wall hanging and having the image of a person, place or thing intended to generate negative emotions in the mind of a user can be provided with an aromatherapeutic agent encapsulated such as within microcapsules, and wherein such microcapsules are layered over at least portions of the image. For purposes of entertainment or even for purposes of therapeutic benefit, an object thrown against the image by a user, such as when in an emotionally agitated state, ruptures at least some of the microcapsules and releases the aromatherapeutic agent, the aromatherapeutic agent being chosen to have a calming aroma. Alternatively, the aromatherapeutic agent can be disposed in or on a projectile and thrown against a wall poster or other object having a disagreeable image or connotation such that an emotionally agitated user throwing the projectile against the image causes the aromatherapeutic agents to be released and to produce a calming affect.

The invention can be otherwise embodied to dispose an aromatherapeutic agent on objects intended to be struck through the agency of a body part of a user or an object manipulated by a user. The object used for striking can alternatively have an aromatherapeutic agent disposed thereon such that a calming aroma is released when the striking object is caused to strike another object. As examples, a mallet used to strike a sounding board can be covered over at least portions of a striking surface of the mallet with a percussively-released aromatherapeutic agent producing a calming aroma being released on striking of the board with the mallet, thereby to reduce an emotional condition causative of the need to strike the board with the mallet. Conversely, the board can be covered over at least certain surfaces thereof with an aromatherapeutic agent so that striking of said surfaces with a mallet or the like releases a calming aroma.

As further exemplary alternatives, an aromatherapeutic agent can be disposed on an object such as a punching bag, a car dashboard, etc., so that manual striking of a surface so covered releases a calming aroma. Accordingly, the disposition of an aromatherapeutic agent over portions of a dashboard of a car or other vehicle and at locations thereof in proximity to an operator of the vehicle such that the operator, when agitated due to the unavoidable emotional insult associated with operation of the vehicle, can strike the covered surface with a hand to thereby release a calming aroma and thus reduce the affects of a condition known as "road rage". The invention finds utility in situations wherein an entertainment benefit and/or therapeutic benefit is desired.

The invention further contemplates the encapsulation of an aromatherapeutic agent, such as within microcapsules or in layers of a polymeric material as an example, with the subsequent disposition of the encapsulated agent on one face of a film or sheet-like substrate, an adhesive such as a low tack adhesive being disposed on the opposite side of the film. The resulting article can then be adhered to a surface of an object such as a wall poster, punching bag, car dashboard, etc., such that the article can be struck with aroma released to provide the benefits herein intended. Through the use of microcapsules in particular, a single percussive event typically ruptures only a portion of the microcapsules, the microcapsule-coated article then being reusable until essentially all of the microcapsules have been ruptured by subsequent percussive events. Once essentially all of the microcapsules have been disrupted, the articles can be readily peeled away and replaced with another article having the same or another aromatherapeutic agent carried by the article. As a further alternative, a substitute configured with microcapsules inter alia can be provided with a release sheet or covering that can be peeled away or otherwise disrupted for release of an aromatherapeutic agent.

Accordingly, it is an object of the invention to provide articles and methods of use of such articles wherein an aromatherapeutic agent is disposed on an object or substrate in a non-aromatic quiescent state so that the substrate can be subjected to a percussive force to release a calming aroma for an entertainment benefit and/or therapeutic benefit.

It is another object of the invention to provide encapsulated aromatherapeutic agents, such as in microcapsules, disposed on one face of a substrate and having an adhesive on another face of the substrate, the substrate being adherable to an object such as a wall poster, punching bag, car dashboard or the like, so that striking of the substrate releases a calming aroma, the substrate being removable and replaceable.

It is a further object of the invention to provide a target and/or projectile for throwing against the target and wherein either or both of the target or the projectile are provided with a normally quiescent aromatherapeutic agent releasable on percussive contact between the target and the projectile, the target preferably having an image formed thereon causative of heightened emotions sufficient to entice a user to throw the projectile against the target.

Further objects and advantages of the invention will become more readily apparent in light of the following detailed description of the preferred embodiments.

BRIEF DESCRIPTION OF THE DRAWINGS

FIG. 9 is a perspective view of a lanyard having an object carried thereby;

FIG. 10 is an idealized perspective view of a spray can directing a spray of aromatherapeutic agent-bearing microcapsules onto a substrate; and, FIG. 11 is a cross-sectional view of a double-sided article having microcapsules containing an aromatherapeutic agent formed on both sides of the article.

DESCRIPTION OF THE PREFERRED EMBODIMENTS

Figure 1:
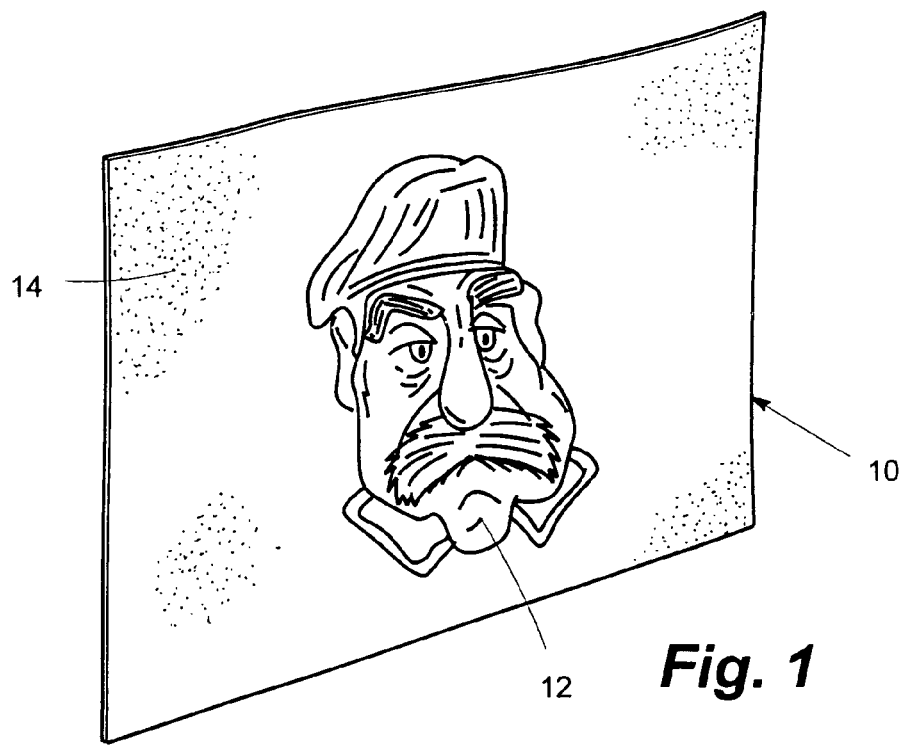
FIG. 1 is a perspective view of a target such as a wall poster having a microencapsulated aromatherapeutic agent provided over at least portions of surfaces thereof.

Referring now to the drawings and particularly to FIGS. 1 through 4, a target 10 is seen to have an image 12 formed on a surface of said target, the target essentially being formed of a sheet of material such as paper, plastic fabric or similar material of the kind used to fabricate posters or the like. The target is conveniently hung on a wall (not shown) in a conventional manner. The target 10 is seen to have an aromatherapeutic agent 14 disposed over an outward face, the aromatherapeutic agent 14 being seen as stippling on the target 10 as represented in the drawings. It is to be understood that the aromatherapeutic agent 14 is intended to be disposed on the target 10 in a manner such that the agent 14 is quiescent, that is, does not emit an appreciably discernable aroma until subjected to a percussive force or other form of activation such as by striking with an object thrown against or otherwise directed against that facing portion of the target 10 having the aromatherapeutic agent 14 disposed thereon. In order to maintain the aromatherapeutic agent in such a condition, the agent 14 can be encapsulated such as with microcapsules formable as one example according to the teachings of U.S. Pat. No. 4,493,869 and patents mentioned in U.S. Pat. No. 4,493,869 inter alia. While thus encapsulated, the aromatherapeutic agent 14 does not emit an aroma. However, when the microcapsules are disrupted, such as by subjection to a percussive force, the aromatherapeutic agent 14 contained within the microcapsules is exposed to the air and emits an aroma intended to have a calming or other affect.

Figure 2:
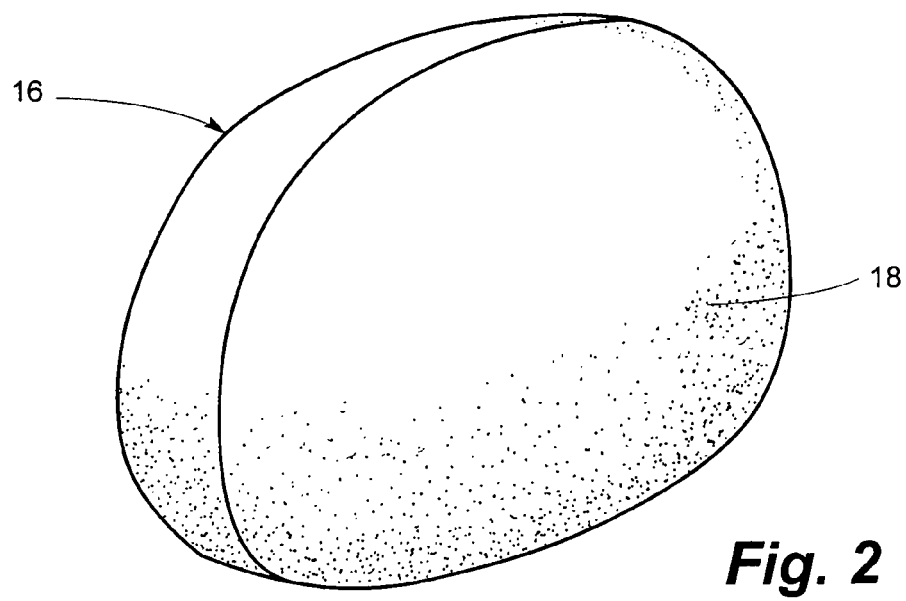
FIG. 2 is a perspective view of a bean bag or similar object which can be manually thrown by a user and having microcapsules containing an aromatherapeutic agent disposed over at least portions of surfaces thereof.

Referring particularly to FIG. 2, a bean bag is seen at 16 to have an aromatherapeutic agent disposed thereon as represented by stippling. It is to be understood that the bean bag 16 can be used as a projectile which could be thrown against the target 10 of FIG. 1 for the purpose of providing the aforementioned percussive effect and to release an aroma from the aromatherapeutic agent 14 disposed on the target 10. When the target 10 is provided with the aromatherapeutic agent disposed thereon, the agent 18 need not be disposed on the bag 16. When the bag 16 has the aromatherapeutic agent disposed thereon, it is not necessary for the agent 14 to be disposed on the target 10. It is further to be understood that both the target 10 and the bag 16 can be used together with both having the respective aromatherapeutic agents 14 and 18 disposed thereon.

Figure 3:
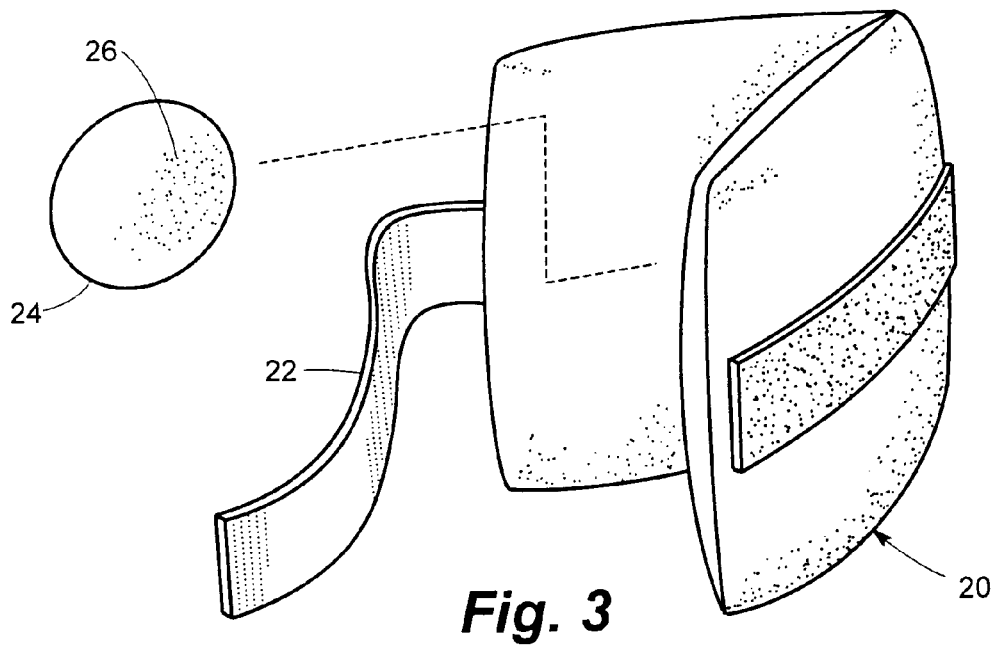
FIG. 3 is an elevational view of a bean bag or similar projectile shown in an unfolded configuration with a disc having microencapsulated aromatherapeutic agents formed thereon.

Referring now to FIG. 3, a bean bag 20 formed in halves is seen to be formable into a projectile through the use of a connector such as a strap 22 having a hook and loop fastening material formed on the strap 22 and on the body of the bag 20 in a manner such as the halves of the bag 20 can be held together. A disc 24 having an aromatherapeutic agent 26 formed on at least some surfaces thereof can be placed between the halves of the bag 20 and held by closure of the bag 20 through the agency of the strap 22. The aromatherapeutic agent 26 can be encapsulated, such as within microcapsules, and caused to adhere to the disc 24 in a manner conventional in the art. The disc 24 can be formed of material such as paper, plastic or the like and can take the form of a planar substrate of any desired geometrical shape. The impact of the bag 20 on a surface when thrown against such a surface, whether or not a surface of the target 10 of FIG. 1, causes release of an aroma from the aromatherapeutic agent 26. The use of a bean bag as an appropriate projectile facilitates aroma release particularly when the aromatherapeutic agent 26 is encapsulated since beans (not shown) contained within the bag 20 move within the confines of the bag 20 and efficiently transfer forces onto the disc and thus onto the encapsulated aromatherapeutic agent 26 when the bag 20 is thrown against an essentially unyielding surface. The act of throwing the bags 16 or 20 against the target 10 or against another surface, especially a surface such as that of the target 10 having an image 12 formed thereon, causes a release of tension which is further enhanced by the aroma of the aromatherapeutic agents 14 or 26. Provision of the image 12 in the form of a person, place of thing against which a user of the target would wish to strike with a projectile provides a further therapeutic affect to the user.

Figure 4:
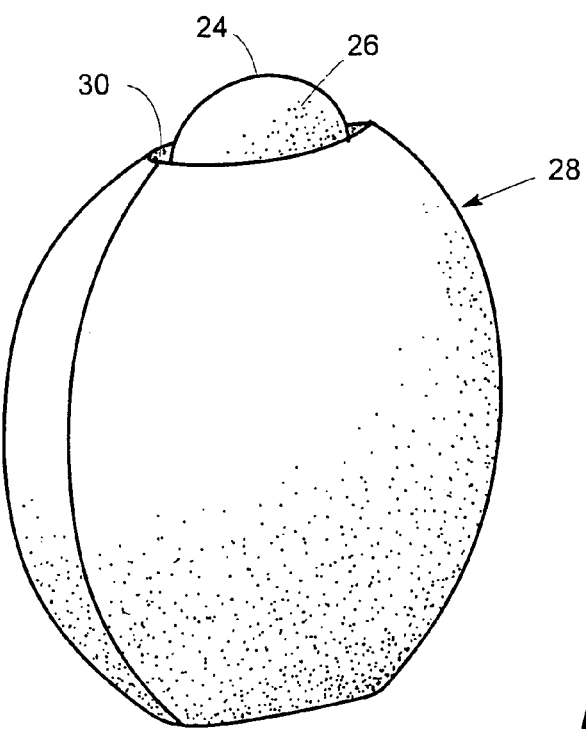
FIG. 4 is a perspective view of a bean bag or other projectile having a pocket into which a disc having microcapsules containing an aromatherapeutic agent is provided.

As is seen in FIG. 4, a bean bag 28 or other suitable projectile can be formed with a pocket 30 within which a disc such as the disc 24 could be placed, the bag 28 then being usable as aforesaid. It is to be understood that the disc 24 can be readily replaced in the bags 20 or 28 when the disc is spent by virtue of disruption of essentially all of the microcapsules containing the aromatherapeutic agents 18 or 26.

Figure 5:
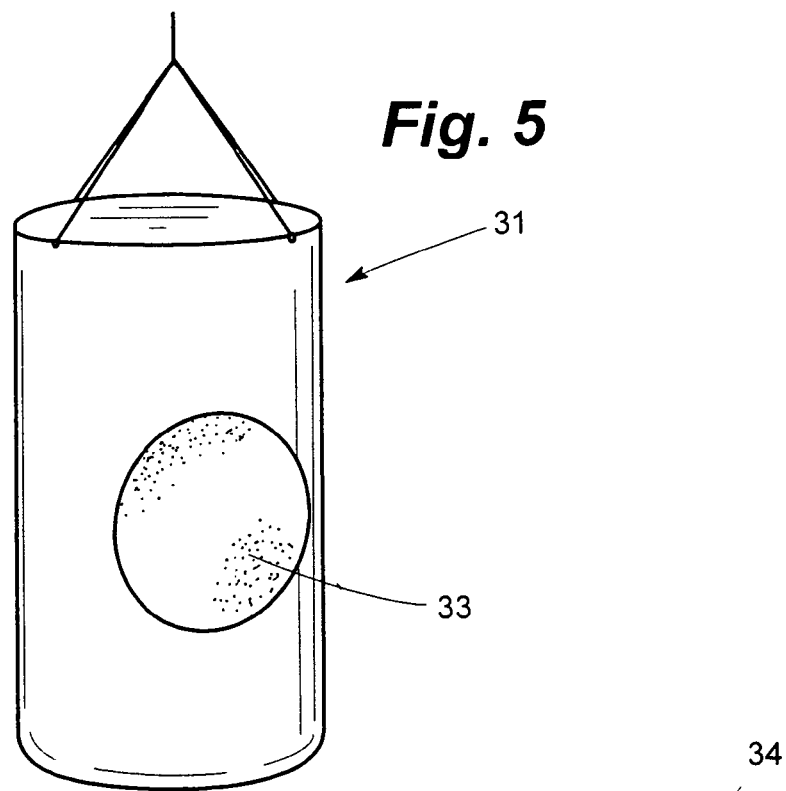
FIG. 5 is an elevational view of a punching bag having microencapsulated aromatherapeutic agents formed on at least portions thereof.

As is seen in FIG. 5, a punching bag 31 is seen to have a disc 33 having microcapsules such as are described herein disposed on one or more of the surfaces of the punching bag 31 as are normally struck by a user. It is to be understood that microcapsules containing an aromatherapeutic agent can be sprayed onto such surfaces such as with an aerosol and from a can or the like.

Figure 6A:
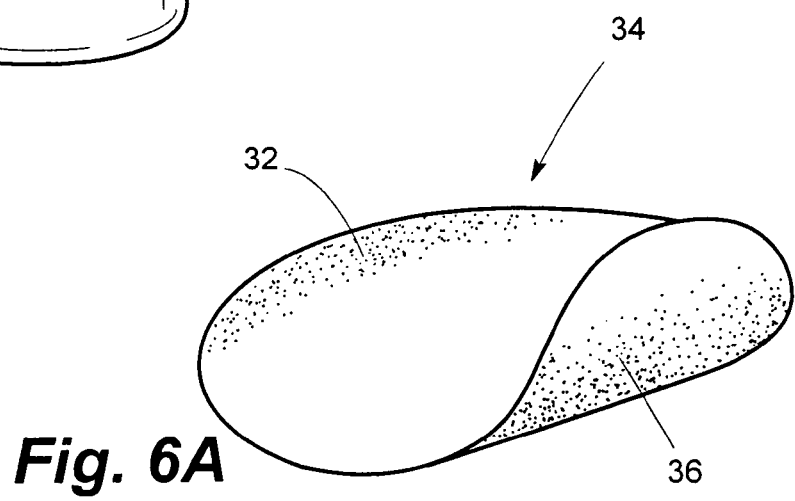
FIG. 6A is a perspective view of an article having microcapsules containing an aromatherapeutic agent formed on one side thereof and an adhesive material formed on the opposite side thereof.
Figure 6B:
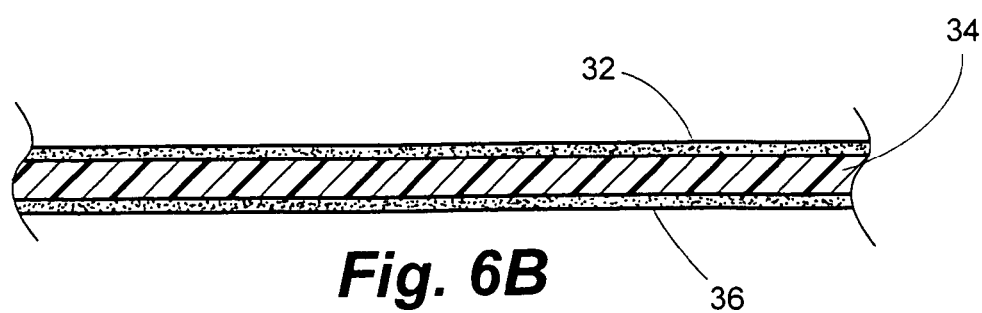
FIG. 6B is a cross-sectional view of the article of FIG. 6A.
Figure 7:
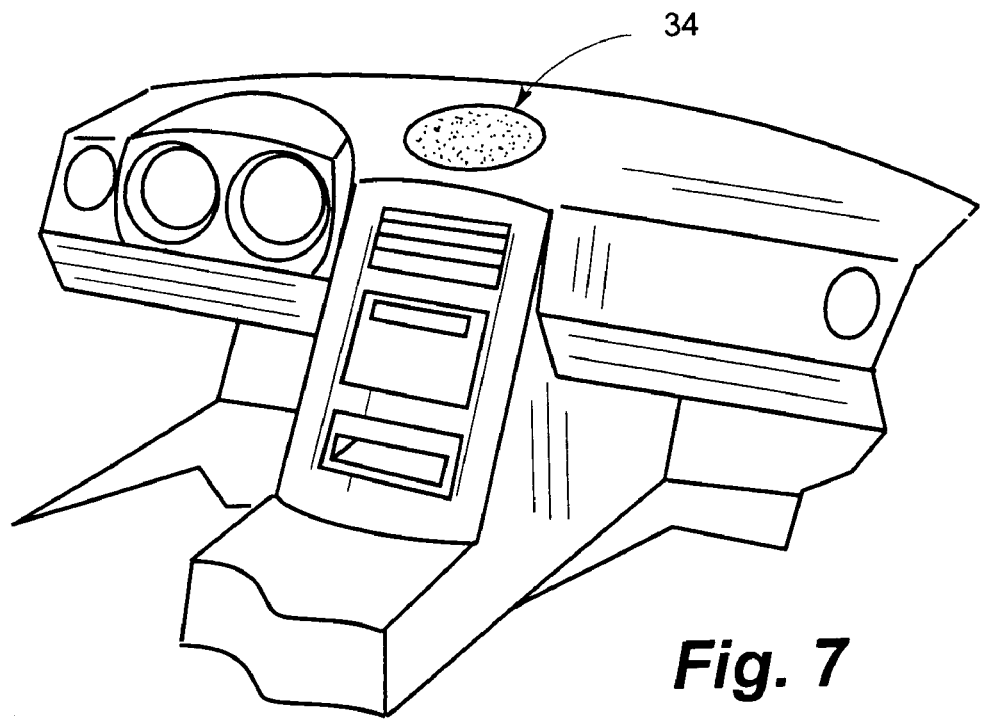
FIG. 7 is a detail perspective view of the article of FIGS. 6A and 6B disposed on the dashboard of a vehicle.

As seen best in FIGS. 6A and 6B, an aromatherapeutic agent usable according to the invention can be encapsulated within microcapsules 32 disposed on a substrate 34, the substrate 34 preferably taking the form of a film or sheet of a material such as paper, plastic or the like. The substrate 34 can be provided with an adhesive layer 36 on the other face of the substrate 34. The adhesive layer 36 is preferably a low tack adhesive such as is conventional in the art and which allows the resulting article to be removably adhered to objects such as a punching bag 38 as seen in FIG. 5 or to a vehicle dashboard or the like as seen in FIG. 7. In such environments, the substrate 34 can be replaced once the microcapsules disposed thereon are all essentially disrupted and the substrate 34 is therefore spent, that is, is not further capable of emitting an aroma when subjected to a percussive force.

Figure 8:
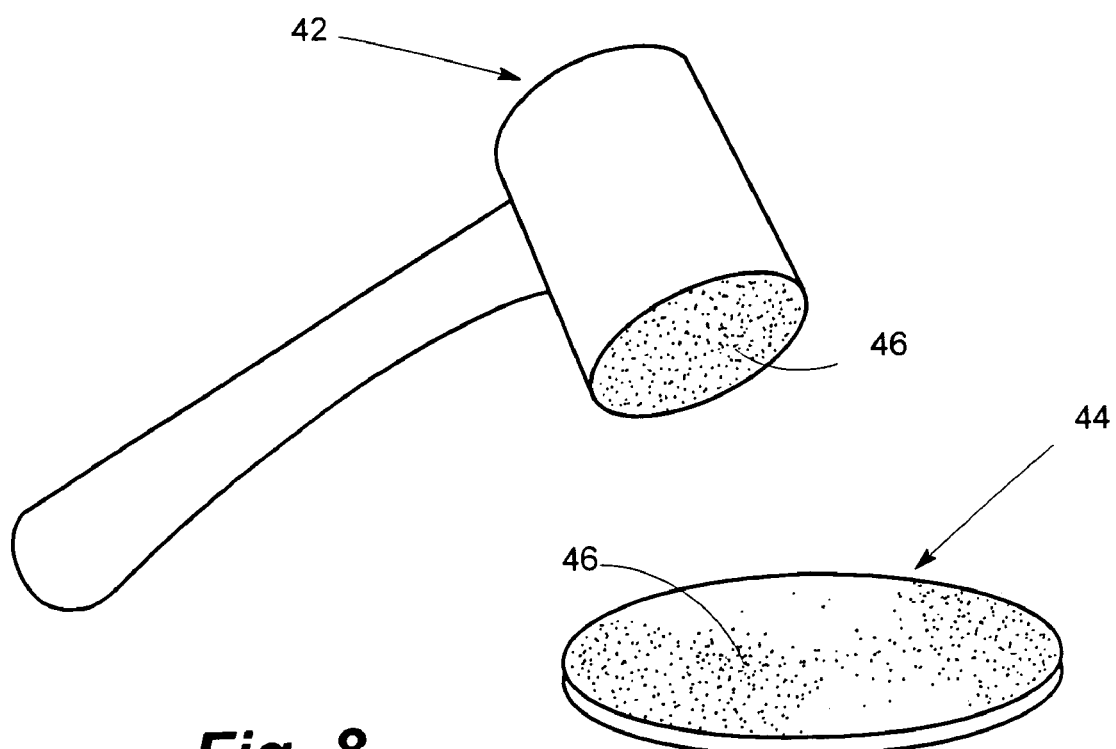
FIG. 8 is a perspective view of a mallet and board intended to be struck by the mallet, the mallet and the board being shown with microcapsules containing an aromatherapeutic agent disposed over surfaces thereof.

In yet another embodiment of the invention as is seen in FIG. 8, a mallet 42 and a sounding board 44 are seen to have an aromatherapeutic agent 46 formed thereon such as on surfaces of the mallet 42 used to strike the board 44 or any other relatively unyielding surface for the purpose of releasing an aroma from the agent 46. The board 44 can be provided with the agent 46 on at least portions thereof, a hammer (not shown) being usable to subject the agent 46 to a percussive force to release the desired therapeutic aroma.

Referring now to FIG. 9, a lanyard 41 such as is conventionally worn about the neck of a user has an object such as a card 43 carried at an end of the lanyard. The card 43 is provided with an aromatherapeutic agent on at least portions of at least one face thereof, the agent being microencapsulated or otherwise provided thereon. The user of the lanyard 41 can take an action necessary to release the agent and thus an aroma depending on the mood of the user. As an example, agents having differing mood influencing properties can be located on different portions of the card 43 with the user releasing the intended aroma to show the mood of the user, each of the agents being indicative of a different mood. The different agents can be disposed on opposite sides of the card 43 with such sides being colored to also show a mood associated with the different mood evoked by the particular agent on the particular side of the card. Cards such as the card 43 and so configured with different colors indicative of mood can be used without association with the lanyard 41 and with a single aromatherapeutic agent disposed thereon as noted above or with more than one agent as described herein. Such cards can be used in games and the like and can be provided in kits with such cards having various colors on faces thereof showing varying moods, the faces of such cards also potentially having holograms and the like disposed thereon and associated with the mood-indicating colors and/or an aromatherapeutic agent or agents disposed on a face or faces of such cards.

FIG. 10 illustrates a spray can 45 directing an aerosol or spray 47 of an aromatherapeutic agent, such as is contained in microcapsules represented by the spray 47, onto a substrate 49. It is to be noted that the agent need not be microencapsulated but is preferably contained such that an aroma is not released by the agent until acted upon such as by directing a percussive force, thereto when on the substrate 49. It is also to be understood that a container or device other than a spray can such as the can 45 can be used to dispense an agent onto a substrate such as the substrate 49.

As seen in FIG. 11, article 48 configured according to another embodiment of the invention is seen to be formed of a sheet-like substrate 50 having an encapsulated or otherwise contained aromatherapeutic agent 52 disposed on both planar faces of the substrate. The article 48 is effectively used within the bags 20 or 28 as examples. A release sheet 54 can be provided over either face of the substrate 50, or both, to permit peeling of said sheet 54 from the substrate to disrupt microcapsules containing an aromatherapeutic agent. Wax or any other suitable coating disruptable to release an aromatherapeutic agent disposed thereunder whether or not encapsulated can also be employed. Articles as are described herein on which a layer of encapsulated aromatherapeutic agent is disposed can thus be provided with a covering release sheet such as the release sheet 54 which may or may not rupture the encapsulations on peeling away of the sheet. In such an application, the aromatherapeutic agent can be disposed on such articles in one or more layers whether or not microencapsulated.

It is to be understood that the invention can be practiced other than as explicitly described herein without departing from the intended scope of the invention as defined by the appended claims.

What is claimed is:

1. A method for producing an entertaining or therapeutic affect in the mind of a user of an aromatherapeutic agent, comprising the steps of:

disposing at least one said aromatherapeutic agent on a substrate, the substrate comprising a target and wherein the agent is disposed on or in the target, the aromatherapeutic agent being contained on the substrate in a condition wherein the agent does not substantially emit an aroma; and, exerting an emotionally driven and forceful percussive action on the aromatherapeutic agent to cause release of an aroma from the agent, the percussive action comprising throwing of an article against that portion of the target on which or in which the agent is disposed, the aroma producing the entertaining or therapeutic affect.

2. The method of claim 1 wherein an aromatherapeutic agent is disposed on or in the article that is to be thrown against the target.

3. The method of claim 1 wherein the target is a poster having an image formed thereon which in the mind of the user would produce a satisfying response in the event of the image being struck by the article under impetus provided by the user.

4. The method of claim 3 wherein the at least one aromatherapeutic agent is disposed on the target in a surmounting relation to the image.

5. The method of claim 1 wherein at least portions of the at least one aromatherapeutic agent is encapsulated within microcapsules rupturable on subjection to the percussive action.

6. The method of claim 1 wherein at least one surface of the substrate has a coloration indicative of a mood intended to be evoked by an aroma emitted by the at least one agent.

7. The method of claim 6 wherein multiple surfaces of the substrate have different colorations each indicative of a mood, each surface differently colored having an agent associated therewith that releases an aroma evocative of the mood associated with the coloration.

8. A method for producing an entertaining or therapeutic affect in the mind of a user of an aromatherapeutic agent, comprising the steps of:

disposing at least one said aromatherapeutic agent on a substrate, the substrate comprising an article wherein the agent is disposed in or on the article, the aromatherapeutic agent being contained on the substrate in a condition wherein the agent does not substantially emit an aroma; and, exerting an emotionally driven and forceful percussive action on the aromatherapeutic agent to cause release of an aroma from the agent, the percussive action comprising throwing of the article by the user to cause release of the aroma, the aroma producing the entertaining or therapeutic affect.

9. The method of claim 8 wherein the user strikes the portion of the article having the agent disposed in or on the article with a second article.

10. The method of claim 8 wherein the agent is encapsulated into discrete quantities of said agent.

11. A method for producing an entertaining or therapeutic affect in the mind of a user of an aromatherapeutic agent, comprising the steps of:

disposing at least one said aromatherapeutic agent on a dashboard or other portion of a vehicle within reach of a user operating the vehicle or being carried by said vehicle, the aromatherapeutic agent being contained on the dashboard or other portion of said vehicle in a condition wherein the agent does not substantially emit an aroma; and, exerting an emotionally driven and forceful percussive action on the aromatherapeutic agent to cause release of an aroma from the agent, the percussive action comprising forcefully striking the dashboard or other portion of said vehicle by the user through the agency of a fist, foot or other portion of the user's body ordinarily used to violently strike an animate or inanimate object, the aroma producing the entertaining or therapeutic affect and having the affect of reducing an emotional condition known as road rage.

12. The method of claim 11 wherein the affect comprises a calming affect.

13. A method for producing an entertaining or therapeutic affect in the mind of a user of an aromatherapeutic agent, comprising the steps of:

disposing at least one said aromatherapeutic agent on a substrate, the substrate comprising a punching bag wherein the agent is disposed in or on the punching bag adapted to be struck by a user, the aromatherapeutic agent being contained on the substrate in a condition wherein the agent does not substantially emit an aroma; and, exerting an emotionally driven and forceful percussive action on the aromatherapeutic agent to cause release of an aroma from the agent, the aroma producing the entertaining or therapeutic affect, the percussive action comprising forcefully striking the punching bag by the user through the agency of a fist, foot or other portion of the user's body ordinarily used to violently strike an animate or inanimate object.

* * * * *